US006777205B1

(12) United States Patent
Carcagno et al.

(10) Patent No.: US 6,777,205 B1
(45) Date of Patent: Aug. 17, 2004

(54) HOST CELLS EXPRESSING RECOMBINANT HUMAN ERYTHROPOIETIN

(75) Inventors: Carlos Miguel Carcagno, Buenos Aires (AR); Marcelo Eduardo Criscuolo, Capital Federal (AR); Carlos Alberto Melo, Buenos Aires (AR); Juan Alejandro Vidal, Buenos Aires (AR)

(73) Assignee: Sterrenbeld Biotechnologie North America, Inc., Wilmington, DE (US)

( * ) Notice: Subject to any disclaimer, the term of this patent is extended or adjusted under 35 U.S.C. 154(b) by 0 days.

(21) Appl. No.: 09/830,967

(22) PCT Filed: Nov. 8, 1999

(86) PCT No.: PCT/US99/26238
§ 371 (c)(1),
(2), (4) Date: Nov. 6, 2001

(87) PCT Pub. No.: WO00/28066
PCT Pub. Date: May 18, 2000

(30) Foreign Application Priority Data

Nov. 6, 1998 (AR) .................................... P98 01 05609
Feb. 23, 1999 (AR) .................................... P99 01 00679

(51) Int. Cl.[7] .......................... C12N 15/12; C12N 5/10; C12P 21/02; C07K 14/505
(52) U.S. Cl. .................... 435/69.1; 435/69.4; 435/471; 435/325; 435/358; 435/360; 435/368; 435/365.1; 435/320.1; 530/350
(58) Field of Search .............................. 435/69.1, 69.4, 435/471, 325, 358, 360, 368, 365.1, 320.1; 530/350

(56) References Cited

U.S. PATENT DOCUMENTS

| | | | |
|---|---|---|---|
| 4,667,016 A | 5/1987 | Lai et al. | 530/397 |
| 4,677,195 A | 6/1987 | Hewick et al. | 530/397 |
| 4,703,008 A | 10/1987 | Lin | 435/240.2 |
| 4,806,524 A | 2/1989 | Kawaguchi et al. | 514/8 |
| 5,010,002 A | 4/1991 | Levinson et al. | 435/69.2 |
| 5,547,933 A | 8/1996 | Lin | 514/8 |
| 5,618,698 A | 4/1997 | Lin | 435/69.4 |
| 5,688,679 A | 11/1997 | Powell | 435/240.2 |
| 5,756,349 A | 5/1998 | Lin | 455/325 |
| 5,783,559 A | 7/1998 | Florin-Robertsson et al. | 514/12 |

FOREIGN PATENT DOCUMENTS

| | | |
|---|---|---|
| WO | WO 86/03520 | 6/1986 |
| WO | WO 98/00530 | 1/1998 |
| WO | WO 00/27419 | 5/2000 |
| WO | WO 00/27869 | 5/2000 |
| WO | WO 00/27997 | 5/2000 |
| WO | WO 00/28066 | 5/2000 |

OTHER PUBLICATIONS

Andersen, D.C. and Goochee, C.F., "The effect of cell–culture conditions on the oligosaccharide structures of secreted glycoprotein," *Curr. Op. Biotech.* 5:546–549, Current Biology Ltd. (1994).

Bondurant, M.C. and Koury, M.J., "Anemia Induces Accumulation of Erythropoietin mRNA in the Kidney and Liver," *Mol. Cell. Biol.* 6:2731–3, American Society for Microbiology (1986).

Borsook, H., et al., "Polycythemic Response in Normal Adult Rats to a Nonprotein Plasma Extract from Anemic Rabbits," *Blood* 9:734–742, Grune and Stratton, Inc. (1954).

Bowie, J.U., et al., "Deciphering the Message in Protein Sequences: Tolerance to Amino Acid Substitutions," *Science* 247:1306–1310, American Association for the Advancement of Science (1990).

Brown, P.R. and Krstulovic, A.M., "Practical Aspects of Reverse–Phase Liquid Chromatography Applied to Biochemical and Biomedical Research," *Anal. Biochem.* 99:1–21, Academic Press, Inc. (1979).

Burg, J., et al., "Human erythropoietin recombinant production by fermentation and protein purification using a series of chromatographic steps," *Chem. Abstracts* 126:315 Abstract No. 57095j, American Chemical Society (1997).

Busuttil, R.W., et al., "The Cytological Localization of Erythropietin in the Human Kidney using the Fluorescent Antibody Technique," *Proc. Soc. Exp. Biol. Med.* 137:327–330, Academic Press, Inc. (1971).

Busuttil, R.W., et al., "Localization of Erythropoietin in the Glomerulus of the Hypoxic Dog Kidney Using a Fluorescent Antibody Technique," *Acta Haemat.* 47:238–242, S. Karger (1972).

Carnot, M.P. and Deflandre, C.. "Sur l'activité hémopïétique 'du sérum au course de la regénération du sang," *C.R. Acad. Sci.* 143:384–386, (1906).

Carnot, M.P. and Deflandre, C., "Sur l'activité hémopïétique des différents organes au cours de la regénération du sang," *C.R. Acad. Sci.* 143:432–435 (1906).

Carnot, M.P., "Sur le Mécanisme de L'hyperglobulie Provoquée par le Sérum D'animaux en Rénovation Sanguine," *C.R.H. Sean. Mem. Soc. Biol.* 111:344–346, Libraries de L'Académie de Médecine (1906).

(List continued on next page.)

Primary Examiner—Elizabeth Kemmerer
Assistant Examiner—Fozia Hamud
(74) Attorney, Agent, or Firm—Sterne, Kessler, Goldstein & Fox PLLC

(57) ABSTRACT

The gene coding for human erythropoietin (EPO) was obtained from human genomic DNA. The gene used does not include sequences from regions at i 5' of the first translated ATG and ii 3' of the stop codon of the EPO gene. The gene was cloned into an expression plasmid for eukaryotic cells that have as sole expression control elements the early promoter of the SV40 virus and its polyadenylation signal. Recombinant cells resulting from transfection with genetic constructs used provide an unexpectedly high level of protein expression of 50 mg of recombinant EPO per liter of culture medium per day.

13 Claims, 4 Drawing Sheets

OTHER PUBLICATIONS

Carnot, M.P., "Sur L'activité Cytopoiétique du Sang et des Organes Régénérés au Cours des Régénérations Viscérales," *C.R.H. Sean. Mem. Soc. Biol. 111*:463–465, Libraires de L'Académie de Médecine (1906).

Caro, J. and Erslev, A.J., "Biologic and immunologic erythropoietin in extracts from hypoxic whole rat kidneys and in their glomerular and tubular fractions," *J. Lab. Clin. Med 103*:922–931, C.V. Mosby Company (1984).

Caro, J., et al., "Erythropoietin Production by an Established Kidney Proximal Tubule Cell Line ($LLCPK_1$)," *Exp. Hematol. 12*:357, Springer–Verlag (1984).

Caro, J., et al., "Erythropoietin in liver tissue extracts and in liver perfusates from hypoxic rats," *Am. J. Physiol. 244*:E431–E434, American Physiological Society (1983).

Dinkelaar, R.B., et al., "Metabolic Studies on Erythropoietin (Ep): II. The Role of Liver and Kidney in the Metabolism of Ep," *Exp. Hematol. 9*:796–803, Allen Press, Inc. (1981).

Dornfest, B.S., et al., "Hepatic production of erythropoietin in a phenylhydrazine–induced compensated hemolytic state in the rat," *J. Lab. Clin Med. 102*:274–85, C.V. Mosby Company (1983).

Dornfest, B.S., et al., "Recovery of an Erythropoietic Inducing Factor from the Regenerating Rat Liver," *Ann. Clin. Lab. Sci. 11*:37–46, Institute for Clinical Science (1981).

Erslev, A., "Humoral Regulation of Red Cell Production," *Blood 8*:349–357, Grune and Stratton, Inc. (1953).

Erslev, A.J., "In Vitro Production of Erythropoietin by Kidneys Perfused With a Serum–free Solution," *Blood 44*:77–85, Gruen and Stratton, Inc. (1974).

Erslev, A.J. and Caro, J., "Physiologic and Molecular Biology of Erythopoietin," *Med. Oncol. Tumor Pharmacother. 3*:159–164, Pergamon Press (1986).

Eschbach, J.W., et al., "Correction of the Anemia of End–Stage Renal Disease with Recombinant Human Erythropoietin," *New Eng. J. Med. 316*:73–78, Massachusetts Medical Society (1987).

Fisher, J.W. and Birdwell, B.J., "The Production of an Erythropoietic Factor by the In Situ Perfused Kidney," *Acta. Haemat. 26*:224–232, S. Karger (1961).

Fisher, J.W., et al., "Localization of Erythropoietin in Glomeruli of Sheep Kidney by Fluorescent Antibody Technique," *Nature 205*:611–612, Macmillian Magazines Ltd. (1965).

Fisher, J.W., "Pharmacologic Modulation of Erythropoietin Production," *Ann. Rev. Pharmacol. Toxicol. 28*:101–122, Annual Reviews, Inc. (1988).

Frenkel, E.P., et al., "Some Observations on the Localization of Erythropoietin," *Ann. N.Y. Acad. Sci. 149*:292–293, New York Academy of Sciences (1968).

Gordon, A.S., et al., "A Plasma Extract with Erythropoietic Activity," *Proc. Soc. Exp. Biol. Med. 86*:255–258, Society for Experimental Biology and Medicine (1954).

Han, F., et al., "Cloning of a human erythropoietin cDNA and its expression in COS–7 cells," *Chem. Abstracts* Abstract No. 511352 (1996).

Hodgson, G. and Tohá, J., "The Erythropoietic Effect of Urine and Plasma of Repeatedly Bled Rabbits," *Blood 9*:299–309, Grune and Stratton, Inc. (1954).

Jacobs, K., et al., "Isolation and characterization of genomic and cDNA clones of human erythropoietin," *Nature 313*:806–810, Macmillan Magazine Ltd. (1985).

Jacobson, L.O., et al., "Role of the Kidney in Erythropoiesis," *Nature 179*:633–634, Macmillan Magazines Ltd. (1957).

Jelkmann, W., et al., "Extraction of Erythropoietin from Isolated Renal Glomeruli of Hypoxic Rats," *Exp. Hematol. 11*:581–588, Allen Press, Inc. (1983).

Jixian, D., et al., "Study on a serum–free medium used for production of rHuEPO," *Bull. Acad. Mil. Med. Sci. 21*:244–246, Academy of Military Medical Sciences (1997).

Kazal, L.A. and Erslev, A.J., "Erythropoietin Production in Renal Tumors," *Ann. Clin. Lab. Sci. 5*:98–109, Institute for Clinical Science (1975).

Krane, N.K., "The Role of Erythropoietin in the Anemia of Chronic Renal Failure," *H. Ford Hosp. Med. J. 31*:177–181, Henry Ford Hospital (1983).

Koury, S.T., et al., "Localization of Erythropoietin Synthesizing Cells in Murine Kidneys by In Situ Hybridization," *Blood 71*:524–527, Grune and Stratton, Inc. (1988).

Koury, S.T., et al., "Quantitation of Erythropoietin–Producing Cells in Kidneys of Mice by In Situ Hybridization: Correlation With Hematocrit, Renal Erythopoietin mRNA, and Serum Erythropoietin Concentration," *Blood 74*:645–651, Grune and Stratton, Inc. (1989).

Kuratowska, Z., et al., "Studies on the Production of Erythropoietin by Isolation Perfused Organs," *Blood 18*:527–534, Grune and Stratton, Inc. (1961).

Kurtz, A., et al., "Renal mesangial cell cultures as a model for study of erythropoietin production," *Proc. Natl. Acad. Sci. USA 80*:4008–4011, National Academy of Sciences (1983).

Lacombe, C., et al., "Peritubular Cells Are the Site of Erythropoietin Synthesis in the Murine Hypoxic Kidney," *J. Clin. Invest. 81*:620–623, Rockefeller University Press (1988).

Liu, P., et al., "Hepatic Erythropoietin (Ep) Production Following Double Partial Hepatectomy in the Rat," *J. Surg. Oncol. 15*:121–132, Alan R. Liss, Inc. (1980).

Naughton, B.A., et al., "Reticuloendothelial System (RES) Hyperfunction and Erythropoietin (Ep) Production in the Regenerating Liver," *J. Surg. Oncol. 12*:227–242, Alan R. Liss, Inc.(1979).

Naughton, B.A., et al., "Evidence for a Hepatic–Renal Antagonism in the Production of Hepatic Erythropoietin," *Ann. Clin. Lab. Sci. 13*:432–438, Institute for Clinical Science (1983).

Parsons, T.F., et al., "Rapid and Easy Separation of the Subunits of Bovine and Human Glycoprotein Hormones by Use of High Performance Liquid Chromatography," *Endocrinology 114:* 2223–2227, J.B. Lippincott Co. (1984).

Reisman, K.R., "Studies on the Mechanism of Erythropoietic Stimulation in Parabiotic Rats During Hypoxia," *Blood 5*:372–380, Grune and Stratton, Inc. (1950).

Schuster, J.H., et al., "Physiologic Regulation and Tissue Localization of Renal Erythropoietin Messenger RNA," *Blood 70*:316–318, Grune and Stratton, Inc.(1987).

Sherwood, J.B., et al., "Erythropoietin Production by Human Renal Carcinoma Cells in Culture," *Endocrinology 99*:504–510, J.B. Lippincott Co. (1976).

Takagaki, Y., et al., "Amino Acid Sequence of the Membranous Segment of Rabbit Liver Cytochrome $b_s$," *J. Biol. Chem. 255*:1536–1541, American Society of Biological Chemists, Inc. (1980).

Werber, M.M., et al., "Preliminary purification of two human blood cell hormones by hydrophobic interaction chromatography," *Chem. Abstracts 100*:77 Abstract No. 203779s, American Chemical Society (1984).

Pending Non–Provisional United States Patent Application No. 09/830,964, Carcagno et al., filed May 3, 2001.

Pending Non–Provisional United States Patent Application No. 09/830,968, Carcagno et al., filed May 3, 2001.

International Search Report of International Application No. PCT/US99/26238, Mar. 7, 2000.

International Search Report of International Application No. PCT/US99/26241, Mar. 7, 2000.

International Search Report of International Application No. PCT/US99/26240, Feb. 22, 2000.

International Search Report of International Application No. PCT/US99/26237, Feb. 18, 2000.

FIG. 4

HOST CELLS EXPRESSING RECOMBINANT HUMAN ERYTHROPOIETIN

This Application claims benefit under 35 U.S.C . § 371 of International Application No. PCT/US99/26238, filed on Nov. 8, 1999, which was published under PCT Article 21(2) in English and which is fully incorporated herein by reference.

BACKGROUND OF THE INVENTION

1. Field of the Invention

The present invention relates, in general, to a host cell and a vector comprising a nucleotide sequence coding for recombinant human etythropoietin (EPO). In particular, the expression vector comprises only one promoter that regulates the EPO expression. The present invention also refers to a method of producing EPO and the EPO thus produced.

2. Background Information

EPO is a glycoprotein that stimulates erythroblast differentiation in the bone marrow, thus increasing the circulating blood erythrocyte count. The mean life of erythrocytes in humans is 120 days and therefore, a human being loses 1/120 erythrocytes each day. This loss must be continuously restored to maintain an adequate level of red blood cells.

The existence of EPO was first postulated by the turn of the century and was definitely proved by Reissman and Erslev early in the '50s. See Carnot, et al., *C.R. Acad. Sci.* (France)143:384–386 (1906); Carnot, et al., *C.R. Acad. Sci.* (France), 143:432–435 (1906); Carnot, et al., *C.R. Soc. Biol.*, 111:344–346 (1906); Carnot, *C.R. Soc. Biol.*, 111:463–465 (1906); Reissman, *Blood*, 5:372–380 (1950) and Erslev, *Blood* 8:349–357 (1953). Reissman and Erslev's experiments were promptly confirmed by other researchers. See Hodgson, et al., *Blood*, 9:299–309 (1954); Gordon, et al., *Proc. Soc. Exp. Biol. Med.*, 86:255–258 (1954) and Borsook, et al., *Blood*, 9:734–742 (1954).

The identification of the EPO production site in the organism was an issue of debate. Successive experiments led to the identification of the kidney as the main organ and peritubular interstitial cells as the synthesis site. See Jacobson, et al., *Nature*, 179:633–634 (1957); Kuratowska, et al., *Blood*, 18:527–534 (1961); Fisher, *Acta Hematol.*, 26:224–32 (1961); Fisher, et al., *Nature*, 205:611–612 (1965); Frenkel, et al., *Ann. N.Y. Acad. Sci.*, 149:292–293 (1968); Busuttil, et al., *Proc. Soc. Exp. Biol. Med*, 137:327–330 (1971); Busuttil, *Acta Haematol.*, (Switzerland), 47:238–242 (1972); Erslev, *Blood*, 44:77–85 (1974); Kazal, *Ann. Clin. Lab. Sci.*, 5:98–109 (1975); Sherwood, et al., *Endocrinology*, 99:504–510 (1976); Fisher, *Ann. Rev. Pharmacol. Toxicol.*, 28:101–122 (1988); Jelkmann, et al., *Exp. Hematol.*, 11:581–588 (1983); Kurtz, et al., *Proc. Natl. Acad. Sci. (USA)*, 80:4008–4011 (1983); Caro, et al., *J. Lab. Clin. Med.*, 103:922–931 (1984); Caro, et al., *Exp. Hematol.*, 12:357 (1984); Schuster, et al., *Blood*, 70:316–318 (1986); Bondurant, et al., *Mol. Cell. Biol.*, 6:2731–2733 (1986); Schuster, et al., *Blood*, 71:524–527 (1988); Koury, et al., *Blood*, 71:524–527 (1988); Lacombe, et al., *J. Clin. Invest.*, 81:620–623 (1988); Koury, et al., *Blood*, 74:645–651 (1989).

A smaller proportion, ranging from 10% to 15% of total EPO, is produced by the liver in adults. See Naughton, et al., *J. Surg. Oncol.*, 12:227–242 (1979); Liu, et al., *J. Surg. Oncol.*, 15:121–132 (1980); Domfest, et al., *Ann. Clin. Lab. Sci.*, 11:37–46 (1981); Dinkelaar, et al., *Exp. Hematol.*, 9:796–803 (1981); Caro, et al., *Am. J. Physiol.*, 244:5 (1983); Dornfest, et al., *J. Lab. Clin. Med.*, 102:274–285 (1983); Naughton, et al., *Ann. Clin. Lab. Sci.*, 13:432–438 (1983); Jacobs, et al., *Nature*, 313:806–810 (1985); Erslev, et al., *Med. Oncol. Tumor. Pharmacother.*, 3:159–164 (1986). The EPO produced is directly proportional to the extent of tisular hypoxia and its expression rises by increasing the number of the EPO producing cells.

EPO has shown great efficiency in the treatment of anemia, especially anemia derived from renal failure. See Eschbach, et al., *N. Enigland J. of Med.*, 316:73–78 (1987); Krane, *Henry Ford Hosp. Med. J.*, 31:177–181 (1983). Its therapeutical usefulness, however, has been limited due to the unavailability of a massive production method. The quantity and quality of the EPO obtained by the extractive systems known were insufficient. Recently, the use of recombinant DNA technology has made it possible to obtain large amounts of proteins. The application of these techniques to eukaryotic cells has allowed a large-scale production of EPO. See patents U.S. Pat. No. 5,688,679 (to Powell), U.S. Pat. No. 5,547,933 (to Lin), U.S. Pat. No. 5,756,349 (to Lin), U.S. Pat. No. 4,703,008 (to Lin) and U.S. Pat. No. 4,677,195 (to Hewick et al.).

At the present, recombinant DNA techniques are widely known and used. These techniques involve the use of genetic elements such as DNA fragments and enzymes to assemble and transfer genetic constructions for the production of recombinant proteins. The recombinant DNA techniques also facilitate the study of biological mechanisms. See Frank-Kamenetskii, "Unraveling DNA" [Samaia Glavnaia Molekula] (Addison Wesley Longman Inc., Reading, Mass., 1997); Brown, "Gene Cloning" (Chapman & Hall, London, England, 1995); Watson, et al., "Recombinant DNA", 2nd Ed. (Scientific American Books, New York, N.Y., 1992); Alberts et al., "Molecular Biology of the Cell" (Garland Publishing Inc., New York, N.Y., 1990); Innis et al., Eds., "PCR Protocols. A Guide to Methods and Applications" (Academic Press Inc., San Diego, Calif., 1990); Ehrlich, Ed., "PCR Technology. Principles and Applications for DNA Amplification" (Stockton Press, New York, N.Y., 1989); Sambrook et al., "Molecular Cloning. A Laboratory Manual" (Cold Spring Harbor Laboratory Press, 1989); Bishop et al., "Nucleic Acid and Protein Sequence. A Practical Approach" (IRL Press 1987); Reznikoff, Ed., "Maximizing Gene Expression" (Butterworths Publishers, Stoneham, Mass., 1987); Davis et al., "Basic Methods in Molecular Biology" (Elsevier Science Publishing Co., New York, N.Y., 1986); Watson, "The Double Helix" (Penguin Books USA Inc., New York, N.Y., 1969).

SUMMARY OF THE INVENTION

The claimed invention comprises an eukaryotic cell line that produces recombinant human EPO, obtained by means of its transfection with an expression vector that comprises a gene coding for human EPO. The vector further comprises an unique promoter and terminator as expression control elements. SEQ ID NO:1 identifies the EPO amino acid sequence codified by the gene used.

The invention provides a host cell comprising a vector which comprises a nucleotide sequence encoding the erythropoietin polypeptide consisting of the amino acid sequence in SEQ ID NO:1, a viral promoter and a viral terminator.

The invention further provides a method for producing an EPO polypeptide, comprising culturing the above host cell under such conditions that said polypeptide is expressed and recovered.

One of the advantages of this invention is that the EPO coding gene utilized does not include non-coding fragments of the 5' and 3' regions. However, the system claimed produces an unexpectedly high amount of EPO.

An additional advantage of this invention is the use of expression vectors comprising only one promoter, which exhibit a high EPO productivity. By utilizing the claimed method, it is possible to obtain more than 50 mg of EPO per liter of cell culture per day, that is, over five times the EPO production level claimed by the best method reported so far utilizing one promoter.

The combination of the EPO coding gene claimed in this invention and a simple promoter showed, surprisingly, to operate efficiently, resulting in a stable EPO producing cell. The transfected cells yielded an amount of EPO comparable to, or even higher than, those reported using in theory more adequate, though more complex and difficult to manipulate, genetic constructions.

An additional advantage of the claimed invention is the cotransfection with two vectors that confer different resistance, thus simplifying and facilitating the selection, genetic amplification and maintenance of the cotransfected EPO producing cells.

Further objects and advantages of the present invention will be clear from the description that follows.

BRIEF DESCRIPTION OF THE FIGURES

FIG. 4 illustrates a survey of the isoelectric points in pure EPO samples produced according to the method described. EPO samples were run in lanes 2, 3 and 4, isoelectric point markers in lanes 1 and 5. The presence of isoforms corresponding to EPO are verified, showing an isoelectric point range of 3.0 to 4.5.

DETAILED DESCRIPTION OF THE INVENTION

Figure 1:
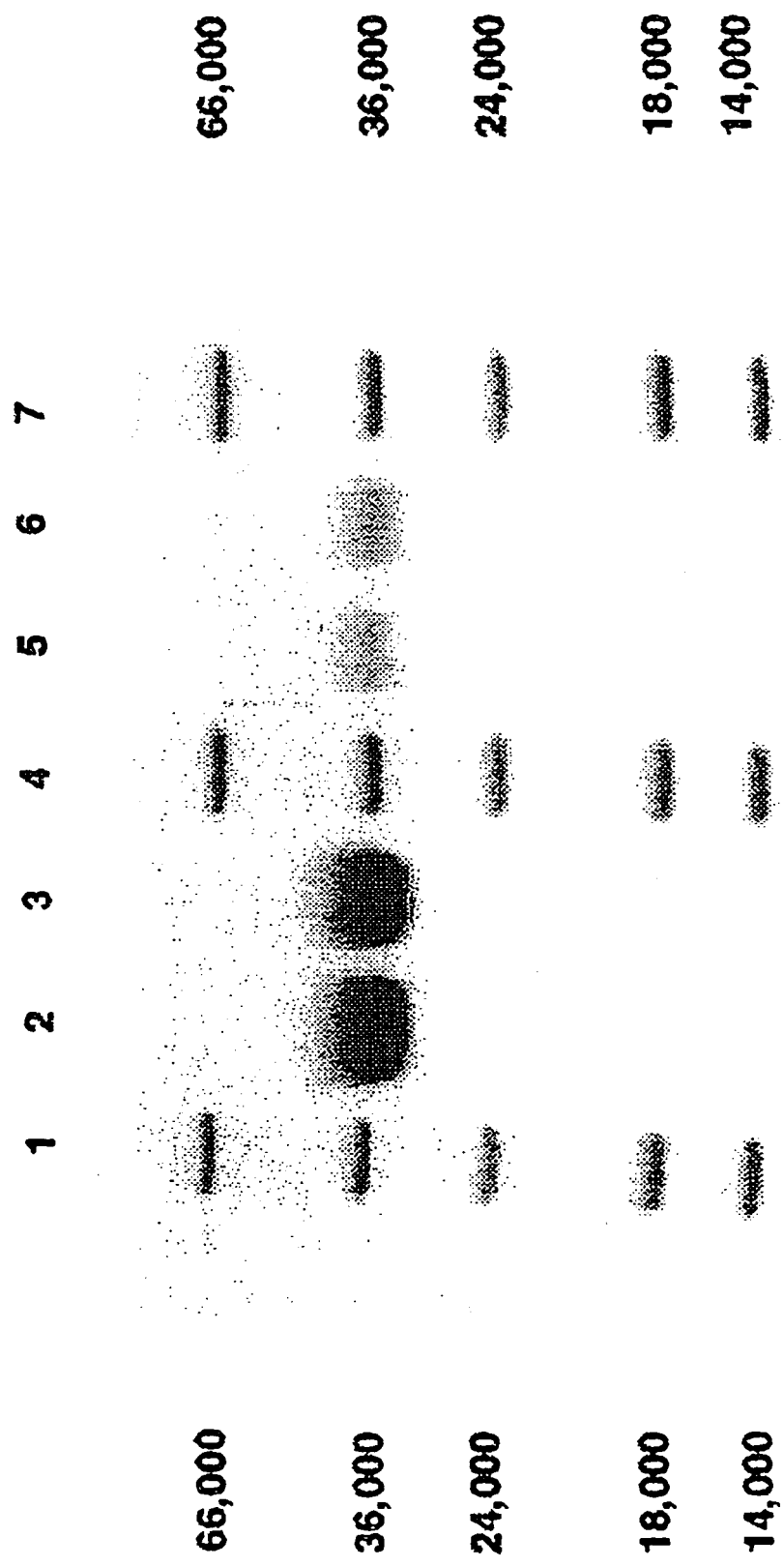
FIG. 1 illustrates polyacrylamide gel (SDS-PAGE) analysis of an EPO sample obtained following the method described after purification. In lanes 1, 4 and 7, molecular weight markers were loaded. In lanes 2, 3, 5 and 6, different amounts of pure EPO obtained according to the claimed procedure were run. The purity of the product obtained and the apparent molecular weight exceeding 30 kDa is coincident with the one reported for urinary human EPO as could be clearly observed.

The biological basis of recombinant DNA technology could be summarized as follows.

DNA (deoxyribonucleic acid) is the genetic material of all living cells and some viruses. Polymeric chains of four different nucleotides form the DNA, each of them being a purine or pyrimidine bound to a desoxyribose. The sugar moiety is in turn linked to a phosphate group. These four nucleotides are: adenine (A), cytosine (C), guanine (G) and thymine (T).

The DNA chains are formed by phosphotriester linkages between nucleotides, where the phosphate in position 5' of the deoxyribose of one nucleotide is bound to the 3' position of the deoxyribose of the previous nucleotide. Synthesis in vivo occurs from 5' to 3', which is the conventional direction adopted to describe DNA sequences.

Functional DNA is presented as a double helix of complementary bases, where chains are held together by hydrogen bonds fomied between A's and C's of one chain and T's and G's of the complementary chain, respectively. This is the reason why they are referred to as "base pairs".

The chains are also antiparallel, that is, the 5' end of each helix is matched to the 3' end of the other, as depicted below:

5'-TACGTAC-3'
3'-ATGCATC-5'

For protein synthesis to occur certain DNA coding regions are first transcribed to messenger RNA (mRNA). The mRNA is translated in turn into a protein. Each of the DNA coding regions is called a gene.

The synthesis of RNA (ribonucleic acid) chains involves the transcription of certain gene regions by enzymes called RNA polymerases. An antiparallel RNA chain, complementary to the DNA template, is thus obtained. Each A from DNA will correspond to a U in the RNA, each C to a G, each G to a C and each T to an A. The RNA molecule is also characterized because it is less stable than DNA. In addition, the sugar moiety in RNA is ribose instead of desoxiribose as in DNA. RNA is further distinguished from DNA by the substitution of uracyl (U) in place of thymine (T).

| Matrix DNA | 5'------------ ACGTAG ------3' |
| Synthesized mRNA | 3'------------ UGCAUC ------5' |

In eukaryotic cells, synthesized mRNA is processed in the nuclei (splicing) to result in mature mRNA. This process is not verified in bacteria.

Mature mRNA is then taken as matrix to be translated into a protein, in a process where transfer RNA (tRNA, small RNA chains that carry amino acids and align them specifically to form a protein) and ribosomes are the main participants. Three mRNA bases (triplet or codon) code each amino acid. For instance, the AUG sequence in mRNA codes for the amino acid methionine. The mRNA chains are thus translated into a specific peptide sequence, which finally folds into an active protein. The protein synthesis is called "expression."

The amount of protein expressed depends, among other factors, on the presence of certain DNA regions called promoters, which affect the rate at which the expression process occurs. In addition, there are DNA sequences that indicate the termination of transcription (terminators) and codons which indicate the end of translation (stop codons).

DNA technology involves the isolation of DNA fragments, either natural or synthetic, and their insertion into cells (i.e. bacteria, yeast, insect and mammalian cells) to render them capable of producing heterologous proteins such as EPO. The proteins obtained by recombinant DNA technology are called recombinant proteins.

The application field of recombinant DNA technology is not limited to cultured cells, since genes can also be incorporated into multicellular organisms (i.e. plants, insects, mammals and fish).

The expression of heterologous proteins requires the following elements:

A gene coding for the desired protein. The gene may be obtained using different techniques, such as;

Isolation from genomic DNA libraries.

In vitro synthesis of DNA chains. There are commercially available equipments that synthesize relatively short DNA strands, making it possible to synthesize a gene in vitro.

Amplification. Technology that allows to replicate several times a DNA fragment, such as a gene.

Others, i.e. as obtained from cDNA libraries synthesized from mRNA.

Active promoters to express a protein in the cell of interest.

Proper terminators so that transcription is correctly terminated.

Vectors. Genetic constructions such as plasmids or viruses that direct the gene with its promoter and terminator towards the inner region of the cell of interest incorporating the gene either in a chromosome or extrachromosomally. In certain cases, the incorporated gene may remain indefinitely in the cell and be transmitted to its progeny, or be lost in a relatively short term. There are multiple vector systems such as plasmids, and natural or modified viruses. It is also possible to use physical means of DNA introduction such as cell or nuclei microinjection. Viruses and plasmids are obtained from nature and are genetically modified in vitro to achieve the desired characteristics.

Others. Additionally, other genetic elements may be necessary to improve the selection of cells receiving the gene (i.e. another gene conferring resistance to antibiotics) or to amplify the number of copies of the gene in each cell (genetic amplification).

Vectors and genes should be as simple as possible to reduce the time necessary to develop the system. A fundamental consideration is that genetic simplicity should not disregard the productivity or quality of the protein produced.

To achieve the expression of the protein of interest, the appropriate corresponding gene is transfected with the proper vectors within the host cell. Transfection may be done by different techniques such as electroporation, precipitation with calcium phosphate and the use of lyposomes, among other techniques available.

The gene of interest may be associated to other genes already known to confer resistance, for instance, to antibiotics such as geneticin, or to toxic agents such as methotrexate (MTX). This association allows the selection of the transfected cells in a stable manner, that is, those selected are capable of reproducing and transmitting the gene of interest to their progeny. Association also permits to select the recombinant cells showing the highest expression level of the protein of interest.

The recombinant product thus obtained is identified by its molecular weight, amino acid sequence and biological activity, among other applicable assays.

The tools (i.e. restriction enzymes) and techniques that gave rise to recombinant DNA technology were first developed in the early '70s and were followed by an intense and widespread utilization. More particularly, the genetic engineering techniques utilized presently to produce EPO involve the following:

1. The use of EPO genes including fragments of non-coding regions located 5' of the first translated ATG and 3' of the stop codon of the gene. It is conventionally believed that the presence of expression control elements located in the non-coding regions of the gene is necessary to achieve a high production of EPO. See patent U.S. Pat. No. 5,688,679 (to Powell).

2. The employment of expression vectors with different promoters, was based upon the premise that a combination of promoters induces a higher EPO production. Until now, the use of only one promoter included in the vector has resulted in a low level of protein expression. See patents U.S. Pat. No. 4,703,008 (to Lin), U.S. Pat. No. 4,677,195 (to Hewick et al.) and U.S. Pat. No. 5,688,679 (to Powell). Average production of EPO using only one promoter is 200 $\mu$/l/day. Maximum production of EPO reported using only one promoter is 10 mg/l/day.

3. The potential instability of the genetic systems due to the complexity of the genetic constructs utilized.

In order to obtain the claimed EPO producing cells, genomic DNA is first extracted from human white blood cells. The EPO coding gene is obtained from the isolated genomic DNA. To achieve this, the gene is amplified using adequate primers to prevent the occurrence of 5' and 3' non-coding regions of the EPO gene. These primers include restriction sites in their 5' ends that remain at both ends of the isolated gene to facilitate further cloning.

The amplified gene is next cloned in a bacterial vector and sequenced. Once the sequence obtained is verified, the gene is cloned into the Xho I-Hind III sites of an expression vector for eukaryotic cells harboring only the SV40 early promoter and its terminator. The vector confers resistance to geneticin and ampicillin.

The CHO cells are subsequently cotransfected with two vectors: 1) the EPO expression vector and 2) a vector that confers resistance to methotrexate. Stably transfected EPO producing cells are selected according to their resistance to geneticin. The level of EPO expression is monitored by the selection of amplified cells resistant to increasing concentrations of methotrexate.

Finally, clones are selected according to their productivity level as measured by radioimmunoassay. Culture supernatants of the most productive clones are used to test the identity of the EPO produced by SDS-PAGE, Western blot, glycanase treatment followed by SDS-PAGE, isoelectric focusing and a complete protein sequence analyses. The biological in vivo activity of the produced EPO is determined by an ex-hypoxic polycythemic mice assay using as reference the international standard for EPO standard.

Vectors and Host Cells

The present invention relates to vectors which include a nucleotide sequence encoding EPO, host cells genetically engineered with the recombinant vectors, and the production of EPO polypeptides or portions thereof by recombinant techniques.

Recombinant constructs may be introduced into host cells using well-known techniques such as infection, transduction, transfection, transvection, conjugation, electroporation and transformation. The vector may be, for example, a phage, plasmid, viral or retroviral vector.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda $P_L$ promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating codon (AUG or GUG) at the beginning and a termination codon appropriately positioned at the end of the polypeptide to be translated.

As indicated, the expression vectors will preferably include at least one selectable marker. More preferably, two expression vectors will include a total of two markers. Such markers include methotrexate, dihydrofolate reductase or neomycin resistance. Preferred vectors confer resistance to methotrexate and neomycin-derived antiobiotics such as genetycin.

Especially preferred host cells are mammalian cells comprising CHO, COS, BHK, Namalwa and HeLa. Preferred host cells are CHO cells. Appropriate culture media and conditions for the above-described host cells are known in the art.

A preferred method of obtaining EPO from the host cells of the invention is culturing in media comprising insulin. Specifically, such culturing comprises separating the supernatant which comprises EPO and insulin from the host cells of the invention, concentrating the supernatant and freezing the concentrated product. Preferably, the culture media comprises between 0.5 mg and 20 mg insulin per liter of culture media.

Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Especially preferred vectors are pDHFR, and pVex 1. The pDHFR vector includes DNA encoding for the dehydrofolate reductase (DHFR) of mouse, whose expression is controlled by the early promoter of the SV40 virus and its polyadenylation signal. The pVex 1-EPO vector comprises the DNA encoding the EPO polypeptide in SEQ ID NO:1, an element conferring resistance to neomycin-derived antibiotics, an early promoter of the SV40 virus and the polyadenylation signal of the SV40 virus.

Suitable eukaryotic promoters for use in the present invention include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter. An especially preferred promoter is the viral SV40 early promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., "Basic Methods in Molecular Biology," (1986).

An especially preferred method to effect introduction of the construct of the invention into a host cell is by calcium phosphate transfection.

Transcription of the DNA encoding the polypeptides of the present invention by higher eukaryotes may be increased by inserting an enhancer sequence into the vector. Enhancers are cis-acting elements of DNA, usually of a size ranging from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, either during purification, or during subsequent handling and storage. Also, peptide moieties may be added to the polypeptide to facilitate purification.

The EPO protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

A preferred method of purifying the EPO produced by the cells of the invention comprises treating cell culture supernatants comprising EPO by a combination of the following steps: (a) differential precipitation, (b) hydrophobic interaction chromatography, (c) diafiltration, (d) anionic exchange chromatography, (e) cationic exchange chromatography and (f) molecular exclusion chromatography. Preferably, said steps are performed in the following order: (a), (b), (c), (d), (e), and (f).

A preferred method of using the EPO produced by the cells of the present invention comprises lyophilization into a form suitable for injection into humans for treatment of disease. Specifically, the preferred lyophilization procedure comprises placing the EPO into a pharmaceutical composition, loading the first EPO composition into a container, wherein said container is at a temperature equal to or less than −30° C.; incubating said EPO composition at a temperature equal to or less than −30° C. under atmospheric pressure for a time equal to or greater than 4 hours; incubating said composition at a pressure of equal to or less than 30 absolute microns for a time equal to or greater than one hour; and raising the temperature equal to or less than 3° C. per hour until reaching at least 25° C., while keeping pressure values equal to or less than 5 absolute microns.

A preferred pharmaceutical composition for lyophilization comprises EPO, sugar, salts and human albumin. An especially preferred composition for lyophilization comprises EPO, mannitol, NaCl, $NaH_2PO_4$ and $Na_2HPO_4 \cdot 12H_2O$.

Nucleic Acid Molecules

The host cells of the present invention may comprise vectors which comprise the EPO nucleic acid molecule from Lin, "DNA Sequences Encoding Erythropoietins," U.S. Pat. No. 4,703,008, which is herein incorporated by reference, and variants thereof. Variants may occur naturally, such as a natural allelic variant. By an "allelic variant" is intended one of several alternate forms of a gene occupying a given locus on a chromosome of an organism. *Genes II*, Lewin, ed. Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Especially preferred among these are silent substitutions, additions and deletions, which do not alter the properties and activities of the EPO protein or portions thereof. Also especially preferred in this regard are conservative substitutions. Most highly preferred are nucleic acid molecules encoding the EPO protein having the amino acid sequence shown in SEQ ID NO:1.

Further embodiments of the invention include isolated nucleic acid molecules comprising apolynucleotide having a nucleotide sequence at least 90% identical, and more preferably at least 95%, 97%, 98% or 99% identical to (a) a nucleotide sequence encoding the EPO polypeptide having the complete amino acid sequence in SEQ ID NO:1 or (b) a nucleotide sequence complementary the nucleotide sequence in (a).

Of course, due to the degeneracy of the genetic code, one of ordinary skill in the art will immediately recognize that a large number of the nucleic acid molecules having a sequence at least 90%, 95%, 97%, 98%, or 99% identical to a nucleic acid sequence encoding the EPO polypeptide will encode a polypeptide "having EPO protein activity." In fact, since all of each and every degenerate variant of these nucleotide sequences encode the same polypeptide, this will be clear to the skilled artisan. It will be further recognized in the art that, for such nucleic acid molecules that are not degenerate variants, a reasonable number will also encode a polypeptide having EPO activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that preserve functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

The invention claimed is better explained by the examples depicted below:

EXAMPLES

Example 1

Preparation of Human Genomic DNA 10 ml of blood were extracted from a clinically healthy human adult male subject and added to a test tube containing 10 mM EDTA (pH 8). The blood was transferred in 5 ml aliquots to two 50 ml test tubes, to which 45 ml of a solution containing 0.3 M of saccharose, 10 mM Tris-HCl (pH 7.5), 5 mM $MgCl_2$ and 1% Triton X 100 was added.

The solutions were then incubated on ice for 10 minutes and centrifuged for 10 minutes at 1,000 g at 4° C. The supernatants were discarded and the pellets rinsed several times with a 0.075 M NaCl solution containing 0.025 M EDTA (pH 8), followed by centrifugation for 10 minutes at 1,000 g at 4° C.

The resulting pellets thus obtained were resuspended in 3 ml of a 10 mM Tris-HCl (pH 8), 400 mM NaCl, 2 mM EDTA (pH 8) solution. 200 μl of 10% SDS (sodium dodecyl sulfate) and 500 μl K proteinase (1 mg/ml in 1% SDS and 2 mM EDTA pH 8) were then added, and the solutions were incubated overnight at 37° C. After the addition of 1 ml of NaCl saturated solution to each test tube the solutions containing the genomic DNA were centrifuged at 2,500 g for 15 minutes.

Each supernatant was transferred to a 15 ml test tube where one volume of isopropanol was added. The test tubes were gently mixed by inversion and stored at room temperature until a DNA precipitate was formed. The genomic DNA was then recovered with a hook-end Pasteur glass pipette.

The DNA was placed in a 2 ml test tube, and 1 ml of 70% ethanol was added. After one minute, the supernatant was discarded and the precipitate was let dry. After drying, the precipitate was dissolved in 500 μl of TE buffer (10 mM Tris-HCl pH 8–1 mM EDTA).

The concentration of the DNA solution was calculated by measuring the absorbance of a 1:1000 dilution of the solution at 260 nm. It was assumed that 50 μg of genomic DNA was equivalent to 1 OD unit. A solution containing 500 ng of genomic DNA per μl of TE buffer was prepared.

Example 2

Preparation of the EPO Construct

The EPO construct was prepared from 500 ng of human genomic DNA obtained in Example 1. The following was added to 1 µl of the solution resulting from Example 1 placed on a 0.5 ml test tube: 400 ng of each of the EPO 1 and EPO 2 primers, an aqueous solution of 2.5 mM of each deoxynucleotide (dATP, dCTP, dGTP and dTTP) and 2.5 units of Taq DNA polymerase (Perkin Elmer) in a final volume of 100 1 using the buffer recommended by the manufacturer. A thermal cycler was used and programmed for 30 cycles of: 1 minute at 93° C., 1 minute at 55° C. and 3 minutes at 72° C. From this reaction, a DNA fragment of approximately 2,170 base pairs containing the EPO gene was obtained.

The nucleotide sequences of the primers utilized were as follows:

EPO 1: 5' GAATTCTCGAGATGGGGGTGCACGGT-GAG 3' (SEQ ID NO:2). This primer corresponds to the first bases which were translated from the EPO gene with a site for the recognition of the Xho I enzyme and another site for the recognition of the Eco RI enzyme in the 5' end. These sites were used in the subsequent cloning steps.

EPO 2: 5' AAGCTTTCATCTGTCCCCTGTCCTGCA 3' (SEQ ID NO:3). This primer is complementary to the last translated bases and the stop codon of the EPO gene. A site for the recognition of the Hind III enzyme was added to the 3' end of the primer. This site was used in subsequent cloning steps.

The nucleotide sequence obtained was as follows (SEQ ID NO:4):

gaattctcgag*atg*ggggtgcacggtgagtactcgcgggctgggcgctcccg-ccgcccgggtccctgtttgagcggggatttagcgcc ccggctattggcca-ggaggtggctgggttcaaggaccggcgacttgtcaaggaccccggaa-ggggaggggtggggcagcctc cacgtgccagcggggacttgggg-gagtccttggggatgg caaaaacctgacctgtgaaggggacacagttt-ggggttgaggggaag aaggtttgggggttctgctgtgcca-gtggagaggaagctgataagctgataacctgggcgctggagccacc-acttatctgccagagggg aagcctctgtcacaccaggattgaagtttggcc-ggagaagtggatgctggtagctgggggtggggtgtgcacacggcag-caggattga atgaaggccagggaggcagcacctgagtgcttgcatggt-tggggacaggaaggacgagctggggcagagacgtggggatgaagga-agctgtccttccacagccaccttctccctccccgcctgactctcagcc-tggctatctgttctagaatgtcctgcctggctgtggcttctcctg tccc-tgctgtcgctccctctgggcctcccagtcctgggcgccccaccacgcc-tcatctgtgacagccgagtcctggagaggtacctcttg gaggccaaggaggccgagaatatcacggtgagacccttccccagcaca-ttccacagaactcacgctcagggcttcagggaactcctc ccagatccaggaacctggcacttggtttggggtggagttgggaagctaga-cactgccccctacataagaataagtctggtggcccaa accatacctgg-aaactaggcaaggagcaaagccagcagatcctacggcctgtgggcca-gggccagagccttcagggacccttgactc cccgggctgtgtgcatttca-gacgggctgtgctgaacactgcagcttgaatgagaatatcactgtccca-gacaccaaagttaatttctatgc ctggaagaggatggaggtgagttcc-tttttttttttttttcctttggagaatctcatttgcgagcctgattttggatgaaa-gggagaatgat cggggaaaggtaaaaggagcagcagagatgaggct-gcctgggcgcagaggctcacgtctataatcccaggctgagatggccgag atgggagaattgcttgagccctggagtttcagaccaacctaggcagcata-gtgagatcccccatctctacaaacatttaaaaaaattagtc aggtgaag-tggtgcatggtggtagtcccagatatttggaaggctgaggcgggagg-atcgcttgagcccaggaatttgaggctgcagtga gctgtgat-cacaccactgcactccagcctcagtgacagagtgaggccctgtctcaaaa-aagaaaagaaaaaagaaaaataatgagggc tgtatggaatacattcat-tattcattcactcactcactcactcattcattcattcattcattcaacaagtct-tattgcataccttctgtttgctcagctt ggtgcttggggctgctgagggca-ggagggagagggtgacatgggtcagctgactcccagagtccactccct-gtaggtcgggcagca ggccgtagaagtctggcagggcctggccctgct-gtcggaagctgtcctgcggggccaggccctgttggtcaactctt-cccagccgtgg gagcccctgcagctgcatgtggataaagccgtcagtgg-ccttcgcagcctcaccactctcttcgggctctgggagccaggtgagtagg agcggacacttctgcttgccctttctgtaagaaggggagaagggtct-tgctaaggagtacaggaactgtccgtattccttcccttctgtgg cactgcagcgacctcctgttttctccttggcagaaggaagccatctcccc-tccagatgcggcctcagctgctccactccgaacaatcactg ctgacactttccgcaaactcttccgagtctactccaatttcctccgggg-aaagctgaagctgtacacaggggaggcctgcaggacaggg gacaga *tga*aagctt The first translated atg codon, as well as the tga "stop" codon, are underlined. The sequences of restriction sites utilized in the cloning are shown in bold italics. It should be noted that more than one codon may code for the same amino acid, and that consequently, the EPO protein could be translated from different mRNA templates having different nucleotide sequences but coding nevertheless for EPO.

Example 3

Cloning and Sequencing of the EPO Gene

A fragment of approximately 2,170 base pairs containing DNA coding EPO was purified. The ends of the DNA were blunted by treatment with the DNA polymerase Klenow's fragment and cloned in the Sma I site of a M13mp18 vector, following standard molecular biology techniques. The recombinant plasmids obtained were cut with Xho I and Hind III enzymes. The presence of the insert was verified by electrophoresis of the restriction fragments in a 0.8% agarose gel stained with ethydium bromide. A positive clone (two bands, one having approximately 2,200 base pairs and the other one corresponding to the linearized vector) were selected. The inserted EPO gene was sequenced according to Sanger's technique using a T7 sequencing kit (Pharmacia). Some regions of the EPO gene were further sequenced with an automatic 370 A Applied Biosystems International sequencer. For each sequencing system the protocols recommended by the manufacturers were followed.

Example 4

Vectors for Eukaryotic Cells

1. Construction of pVex 1 Vector

The pVex1 vector was built following the standard molecular biology teclniques. It consisted of:

a. Fragments of the bacterial pBR322 vector, which have a bacterial replication origin and confer resistance to ampicillin, for amplification and selection of the vector in *E. coli*.

b. Immediately downstream from a) follows an early promoter of the SV40 virus, which allowed the expression of the genes cloned at 3' from this element.

c. Immediately downstream from b) follow the Xho I and Hind III cloning sites, which allowed the insertion of the genes to be expressed.

d. Immediately downstream from c) follows the polyadenylation signal of the SV40 virus, which allowed the proper polyadenylation of the specific transcripts of the gene cloned in c).

e. Immediately downstream from d) follow the TK promoter and the gene coding for neomycin phosphotransferase with its polyadenylation signal. These elements allowed the selection of stably transfected cells through the use of neomycin and neomycin-derived antibiotics such as geneticin. The 3' end of e) is linked to the 5' end of a).

The pVex 1 vector was deposited on Apr. 16, 1999 at DSMZ-Deutsche Sammlung von Mikroorganismen und Zellkulturen GmbH, Mascheroder Weg 1 b, D-38124 Braunschweig, Germany, and was given accession number DSM 12776.

2. pDHFR Vector

The pDHFR vector confers resistance to ampicillin for selection in bacteria. This vector includes the cDNA coding for mice dihydrofolate reductase (DHFR), whose expression level is controlled by the SV40 virus early promoter and its polyadenylation signal. The EPO expression level achieved with the pVex 1-EPO (See Example 5) vector is enhanced several times by the amplification of the DHFR and EPO genes in a culture medium containing increasing concentrations of methotrexate (MTX).

The pDHFR vector was deposited on Apr. 16, 1999 at DSMZ-Deutsche Sammlung von Mikroorganismen und Zellkulturen GmbH, Mascheroder Weg 1 b, D-38124 Braunschweig, Germany, and was given accession number DSM 12777.

Example 5
Cloning of the EPO Coding Gene into an Expression Vector

The M13mp18 clone containing the EPO coding gene cloned as described in Example 3 was cut with Xho I-Hind III enzymes. The fragment thus obtained, of approximately 2.2 Kb, was isolated and cloned again using the same restriction sites of the pVex I vector. A positive pVex-EPO clone was isolated and analyzed showing that the EPO coding sequence SEQ ID NO:4 did not change during the cloning procedures.

The previous examples were performed according to conventional molecular biology techniques. See Brown, "Gene Cloning", (Chapman & Hall, London, England, 1995); Watson, et al., "Recombinant DNA, $2^{nd}$ Ed.", (Scientific American Books, New York, N.Y., 1992); Sambrook et al, "Molecular Cloning. A Laboratory Manual", (Cold Spring Harbor Laboratory Press, 1989); Bishop et al., "Nucleic Acid and Protein Sequence. A Practical Approach", (IRL Press, 1987); Davis et al., "Basic Methods in Molecular Biology", (Elsevier Science Publishing Co., New York, N.Y., 1986).

Example 6
Co-transfection and Amplification

A mutagenized CHO (Chinese Hamster Ovary) cell line, deficient in the DHFR-enzyme gene (CHO-DHFR$^-$), was used to facilitate gene amplification with MTX. During the entire process cells were grown in a 5% $CO_2$ atmosphere at 37° C.

The CHO cells were cotransfected following the calcium phosphate technique which, using a 90 mm diameter Petri dish, was as follows:

(1) The culture medium (alpha-MEM, with 10% of fetal calf serum) was replaced with fresh medium 4–8 hours before transfection.

(2) 500 $\mu$L of 10 g/l HEPES (pH 7.1) solution, 500 $\mu$L of 16 g/l NaCl, 10 $\mu$l of a 35 mM $Na_2HPO_4$ and 10 $\mu$l of 35 mM of $NaH_2PO_4$ solution were added to a 5 ml test tube.

(3) In a separate 1.5 ml test tube, a solution with 60 $\mu$l of 2 M $CaCl_2$ and 10 $\mu$g of each DNA vector to be transfected (pVex-EPO and pDHFR) were added. Water was added until a final volume of 500 $\mu$l was reached. The pDHFR plasmid described in Example 2 is based on the pBR 322 plasmid, which is ampicillin-resistant. The pDHFR plasmid can be replicated in *E. Coli* and has the DHFR gene cloned between the SV40 early promoter and its terminator. The pDHFR plasmid codes for the expression of the DHFR protein in CHO cells. This protein confers resistance to methotrexate, which can then be used to select cells showing high erythropoietin productivity.

(4) The solution containing DNA and $CaCl_2$ was added drop by drop to the test tube containing HEPES, while air was bubbled to obtain a rapid mixing and minimize local concentration. This method facilitated the formation of very small particles containing DNA and calcium phosphate which are more effectively incorporated by the cells.

(5) The solution was allowed to settle for 30 minutes and was added then to the Petri dish containing the cells.

(6) The solution was distributed among the cells by gentle shaking. The cells were left overnight in an incubator under a 5% $CO_2$ atmosphere at 37° C.

(7) Cells were rinsed twice with a PBS buffer (8 g NaCl; 0.2 g KCl; 1.44 g $Na_2HPO_4$, 0.24 g $NaH_2PO_4$, water was added to 1 liter and pH was adjusted to 7.4 with HCl). Fresh culture medium was then added.

The selection with geneticin (G 418) at a concentration of 600 g/ml begun 24 hours after transfection. The cells which incorporated the pVex-EPO plasmid were able to resist the antibiotic, while all others died after 25 days. Resistant colonies were selected and their productivity was assayed. The three most productive clones were selected from the isolated clones.

Taking advantage of the genetic constructions used in the invention, a selection was performed for each of the three clones using MTX as secondary selective agent at a $10^{-8}$ M, $10^{-7}$ M, $10^{-6}$ M and $10^{-5}$ M concentration. For that purpose, the culture medium was changed to alpha-MEM without nucleotides, supplemented with 10% dialyzed fetal calf serum. It is essential to perform the dialysis process according to the following protocol: 100 ml of serum were placed in a dialysis bag with a 3,000 Da cut off (with a higher cut off, growth factors could be lost, and the cells would not be able to grow and reproduce), the bag was hermetically closed, completely immersed in a container with 5 liters of bidistilled water and left without agitation for 12 hours at 4° C. After this step, the water was discarded and changed, leaving the bag to stand for an additional 12 hour period at 4° C. The dialysis bag was then removed and the serum recovered. The dialysis during shorter periods, with smaller volumes or without water replacement, would be ineffective since any trace of nucleotides in the serum will affect the MTX selection adversely. In the other hand, dialysis for longer periods would also be ineffective because some proteins necessary for cell growth may precipitate preventing cell maturation.

Example 7
Isolation of High Productivity Clones

Clones that grew in $10^{-7}$ and $10^{-6}$ M of MTX were isolated and amplified in fresh alpha-MEM without nucleotides supplemented with 10% of dialyzed fetal calf serun. Once grown, the culture supernatant was assayed for the production and secretion of EPO. For that purpose, a specific immunoassay was used.

The process described above concluded with the selection of a clone of recombinant host cells producing 50,000 $\mu$g of erythropoietin/liter of culture medium per day.

The recombinant host cell described in this example was deposited on Apr. 16, 1999 at DSMZ-Deutsche Sammlung von Mikroorganismen und Zellkulturen GmbH, Mascheroder Weg 1b, D-38124 Braunschweig, Germany and given accession number DSM ACC2397.

The effectiveness of transcription process in the cell was verified as described in Example 8. The sequence of the obtained protein was identified following the procedure described in Example 9.

Example 8
Verification of the Specific Messenger RNA Sequence Produced by the Reconmbinant Cells 1. Preparation of RNA from Cells Total RNA was prepared from EPO producing cells, according to the following protocol:

A 90 mm diameter Petri dish having confluent cells was washed twice with 10 ml of PBS buffer. 2 ml of GTC buffer were then added and distributed evenly over the dish. The GTC buffer was composed of: 50 g guanidinum thiocyanate; 0.5 g N-Lauroylsarcosine, 2.5 ml 1 M sodium citrate (pH 7), 0.7 ml β-mercapthoethanol, 0.33 ml of 30% antifoam agent (SIGMA) and 100 ml $H_2O$ q.s. (pH 7.0).

Cells were then lysed. The lysate resulted in a highly viscous solution. The solution was transferred to a 15 ml test tube, and the process above described was repeated once more using 2 ml of GTC buffer.

The 15 ml test tube was vigorously stirred for 1 minute to break the DNA. A cesium chloride gradient was then performed. For that purpose, 4 ml of a solution containing CsCl (95.97 g CsCl and 2.5 ml of 1 M Sodium acetate, (pH 5.4), and water was added until a volume of 100 ml was reached) were added to an ultracentrifuge test tube. Overthis solution and without mixing, the suspension of the cells in GTC was then added. The test tube was next filled with GTC buffer and ultracentrifuged at 31,000 rpm for 20 hours at 20° C.

During centrifugation, the RNA was deposited at the bottom of the test tube forming a pellet and the DNA obtained showed a band in the middle of the cesium chloride gradient. The supernatant was discarded to eliminate thoroughly the DNA. The RNA-containing pellet was let dry for 5 minutes and was dissolved then in 200 μl of water and transferred to a 1.5 ml test tube. 200 μl of 0.4 M Sodium acetate, (pH 4.8) and 2 volumes of ethanol were then added, the resulting solution was thoroughly mixed and left to settle for 30 minutes at −80° C. The solution was then centrifuged in a microcentrifuge at 14,000 rpm for 15 minutes, the supernatant was discarded and the precipitate was rinsed with 1 ml 80% ethanol. The pellet was dried and redissolved in 100 μl of water. The concentration of a 1:100 dilution of the RNA solution was measured at 260 nm (1 OD unit corresponds approximately to 40 μg of RNA). All the solutions and elements used were RNase-free.

2. Preparation of cDNA

Specific cDNA was prepared following the directions of a kit intended for that purpose (cDNA Synthesis System Plus, Amersham—cat. RPN 1256). The EPO 2 oligonucleotide was the primer used.

3. Cloning of cDNA Coding for EPO

Five percent of the cDNA thus obtained was amplified using 400 ng of each the EPO 2 and EPO 3 oligonucleotides, 2.5 mM of each deoxynucleotide in the proper buffer, and 2.5 units of Taq DNA polymerase, in a total volume of 100 μl. 35 amplification cycles were performed as follows: 1 minute at 93° C., 1 minute at 55° C. and 1 minute at 72° C.

EPO 3 was synthesized as described for EPO 1 and EPO 2, and its sequence (5' GAATTCCATGGGGGTGCAC-GAATGTCC 3') (SEQ ID NO:5) corresponded to the first 20 bases coding for the EPO cDNA, and one site for the recognition of the Eco RI enzyme. The Eco RI enzyme recognition site was added to facilitate subsequent cloning steps.

A fragment of approximately 600 base pairs was obtained and cloned in M13mp18 and M13mp19 vectors. Using the Sanger's sequencing method, the insert was sequenced in both directions to obtain the complete sequence.

Due to the high autocomplementarity of some regions of the gene, which gives rise to many and very ambiguous compressions in the autoradiography, a sequencing kit using Taq DNA polymerase and modified bases was used. Lower quality results were obtained, but the compressions were resolved. The kit used was the Pharmacia-LKB Biotechnology Gene aTaq.

The complete sequence of the human erythropoietin cDNA was isolated and cloned, showing to code for EPO. Consequently, the gene cloned in the cells and its transcription product were found complete and its sequence correct for EPO.

Example 9
Analysis of the EPO Produced

The EPO obtained by culturing the host cells as illustrated in the preceding example was further purified to undergo various quality and identificatory assays.

Figure 2:
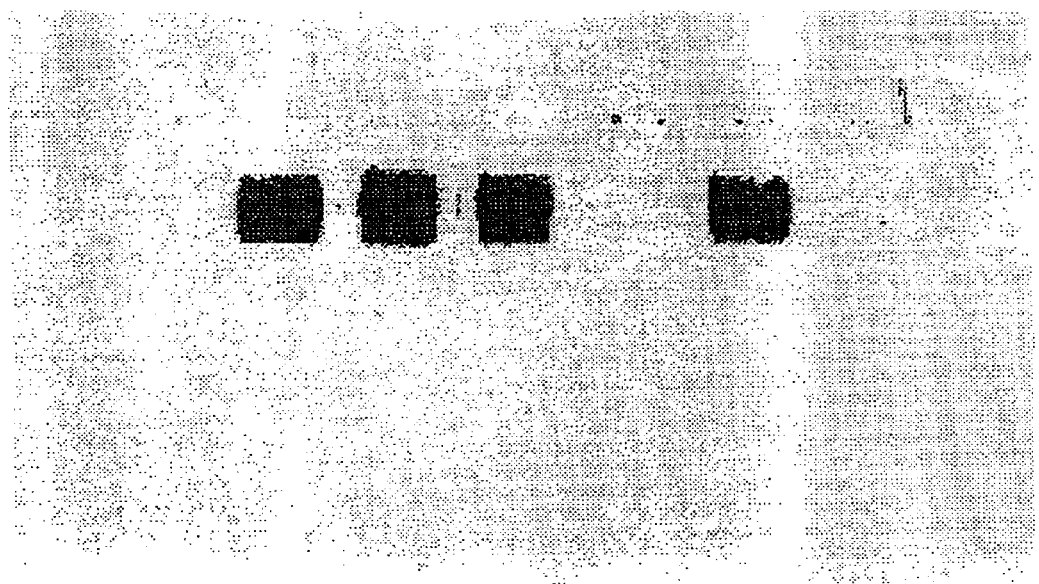
FIG. 2 illustrates a Western blot analysis of an EPO sample obtained according to the method described. Identity of the EPO produced is assessed, since it is recognized by a monoclonal antibody against human EPO. In lanes 1 and 2, a human EPO standard and molecular weight markers were loaded, respectively. EPO samples obtained according to the claimed method were loaded in lanes 3 to 5.
Figure 3:
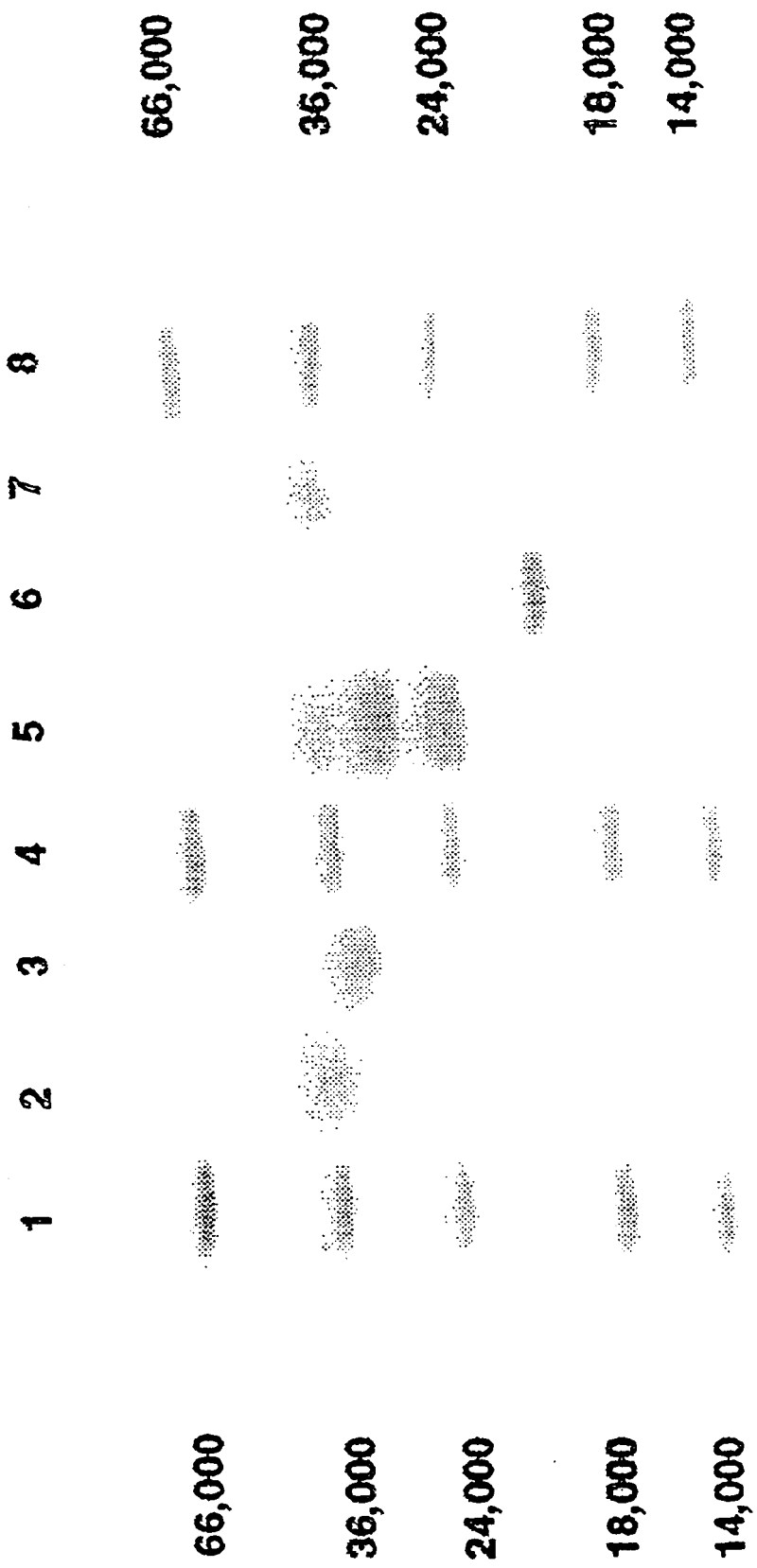
FIG. 3 shows a SDS-PAGE analysis of a pure EPO sample obtained according to the method described, and further treated with glycanases. Molecular weight markers were loaded in lanes 1, 4 and 8. Lanes 2 and 7 correspond to untreated EPO. In lane 3, O-glycanase treated EPO was loaded; the presence of an O-glycosilation site is verified. In lane 5, N-glycanase partially digested EPO was loaded. The presence of 3 N-glycosilated molecules with molecular weights as expected for EPO can be verified. Lane 6 was loaded with EPO digested with N-glycanase, and the expected molecular weight for the wholly deglycosilated protein was obtained.
Figure 4:
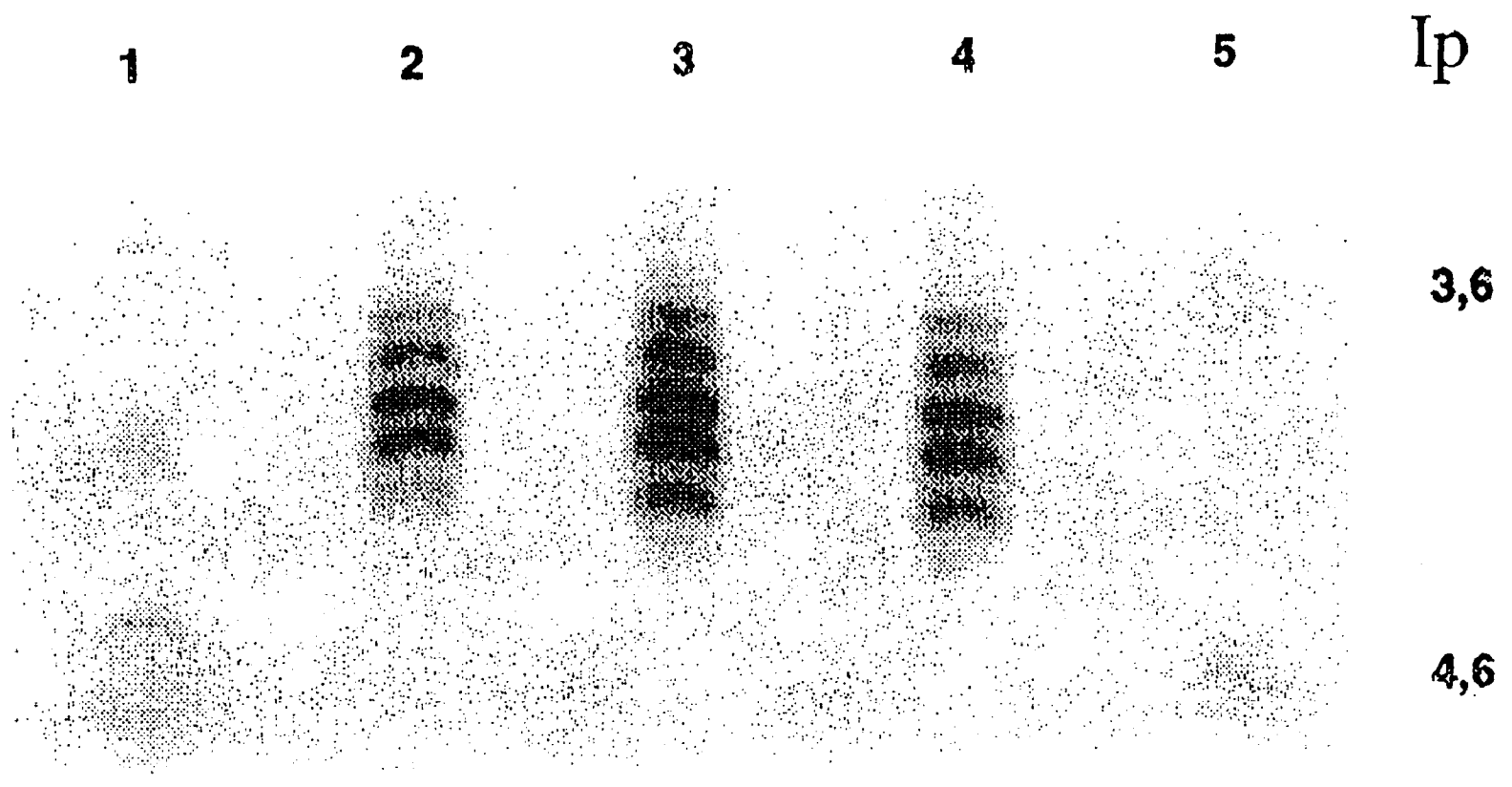

In a denaturing SDS-PAGE gel the EPO was identified as a wide band of molecular weight over 30 kDa as expected for EPO. See FIG. 1. The band was recognized by monoclonal and polyclonal antibodies against human EPO in a "Western blot" assay as expected for EPO. See FIG. 2. The treatment with glycanases proved the existence of the glycosidic chains in the extent and size as expected for EPO. See FIG. 3. The EPO produced was shown to be composed of a series of species ranging isoelectric points from 3.0 to 4.5 as expected for EPO. See FIG. 4.

The complete amino acid sequence of the isolated protein, purified from the culture supernatant of transfected cell lines showed total homology with natural human crythropoietin whose 165 amino acid sequence is as follows (SEQ ID NO:1):

```
NH2---Ala Pro Pro Arg Leu Ile Cys Asp

Ser Arg Val Leu Glu Arg Tyr Leu

Leu Glu Ala Lys Glu Ala Glu Asn

Ile Thr Thr Gly Cys Ala Glu His

Cys Ser Leu Asn Glu Asn Ile Thr

Val Pro Asp Thr Lys Val Asn Phe

Tyr Ala Trp Lys Arg Met Glu Val

Gly Gln Gln Ala Val Glu Val Trp

Gln Gly Leu Ala Leu Leu Ser Glu

Ala Val Leu Arg Gly Gln Ala Leu

Leu Val Asn Ser Ser Gln Pro Trp

Glu Pro Leu Gln Leu His Val Asp

Lys Ala Val Ser Gly Leu Arg Ser

Leu Thr Thr Leu Leu Arg Ala Leu

Gly Ala Gln Lys Glu Ala Ile Ser

Pro Pro Asp Ala Ala Ser Ala Ala

Pro Leu Arg Thr Ile Thr Ala Asp

Thr Phe Arg Lys Leu Phe Arg Val

Tyr Ser Asn Phe Leu Arg Gly Lys

Leu Lys Leu Tyr Thr Gly Glu Ala

Cys Arg Thr Gly Asp----COOH
```

The presence of the four glycosilation sites along the 165 amino acid chain, as well as the complex carbohydrate structure, and in particular, the sialic acid terminal residues, which characterize EPO were verified. These results were further supported by a biological activity assay of the produced protein by an ex-hypoxic polycythemic mice test which showed complete concordance with the international EPO standard.

The productivity achieved, measured by a specific immunoassay, was 50 mg EPO per liter of culture medium per day.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated host cell comprising a vector which comprises:
   (a) a nucleotide sequence encoding the erythropoietin polypeptide consisting of the amino acid sequence in SEQ ID NO:1 wherein said nucleotide sequence does not include non-coding fragments from 5' and 3' regions;
   (b) a viral promoter; and
   (c) a viral terminator.

2. The host cell deposited as DSM ACC2397.

3. The host cell of claim 1, wherein said viral promoter and viral terminator comprises an early promoter and terminator of a SV40 virus.

4. The host cell of claim 1, wherein said vector comprises pVex 1 deposited as DSM 12776.

5. The host cell of claim 1, further comprising a pDHFR vector.

6. The host cell of claim 4, wherein said host cell is resistant to neomycin-derived antibiotics and methotrexate.

7. The host cell of claim 1, wherein said host cell is a mammalian cell.

8. The host cell of claim 7, wherein said mammalian cell is selected from the group consistng of CHO, COS, BHK, Namalwa, HeLa, Hep3B and Hep-G2 cells.

9. The host cell of claim 1, wherein said host cell comprises a CHO or COS cell.

10. The host cell of claim 1, wherein said host cell comprises a CHO cell.

11. A method for producing an EPO polypeptide, comprising culturing the host cell of claim 1 under conditions such that said polypeptide is expressed and recovered.

12. The method of claim 11, wherein such conditions comprise exposure to methotrexate.

13. The method of claim 11, wherein said culture produces more than 50 mg of EPO per liter of culture medium per day.

* * * * *

SEQUENCE LISTING

```
<160> NUMBER OF SEQ ID NOS: 5

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 2
gaattctcga gatgggggtg cacggtgag                                         29

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 3
```
aagctttcat ctgtccctg tcctgca                                        27

<210> SEQ ID NO 4
<211> LENGTH: 2164
<212> TYPE: DNA
<213> ORGANISM: Homo sapiens

<400> SEQUENCE: 4

| | | | | | |
|---|---|---|---|---|---|
| gaattctcga | gatggggtg | cacggtgagt | actcgcgggc | tgggcgctcc | cgccgcccgg | 60 |
| gtccctgttt | gagcgggat | ttagcgcccc | ggctattggc | caggaggtgg | ctgggttcaa | 120 |
| ggaccggcga | cttgtcaagg | accccggaag | ggggaggggg | gtggggcagc | ctccacgtgc | 180 |
| cagcggggac | ttgggggagt | ccttgggat | ggcaaaaacc | tgacctgtga | agggacaca | 240 |
| gtttggggt | tgagggaag | aaggtttggg | ggttctgctg | tgccagtgga | gaggaagctg | 300 |
| ataagctgat | aacctgggcg | ctggagccac | cacttatctg | ccagagggga | agcctctgtc | 360 |
| acaccaggat | tgaagtttgg | ccggagaagt | ggatgctggt | agctggggt | gggtgtgca | 420 |
| cacggcagca | ggattgaatg | aaggccaggg | aggcagcacc | tgagtgcttg | catggttggg | 480 |
| gacaggaagg | acgagctggg | gcagagacgt | ggggatgaag | gaagctgtcc | ttccacagcc | 540 |
| acccttctcc | ctccccgcct | gactctcagc | ctggctatct | gttctagaat | gtcctgcctg | 600 |
| gctgtggctt | ctcctgtccc | tgctgtcgct | ccctctgggc | ctcccagtcc | tgggcgcccc | 660 |
| accacgcctc | atctgtgaca | gccgagtcct | ggagaggtac | ctcttggagg | ccaaggaggc | 720 |
| cgagaatatc | acggtgagac | cccttcccca | gcacattcca | cagaactcac | gctcagggct | 780 |
| tcagggaact | cctcccagat | ccaggaacct | ggcacttggt | ttggggtgga | gttgggaagc | 840 |
| tagacactgc | cccctacat | aagaataagt | ctggtggccc | caaaccatac | ctggaaacta | 900 |
| ggcaaggagc | aaagccagca | gatcctacgg | cctgtgggcc | agggccagag | ccttcaggga | 960 |
| cccttgactc | cccgggctgt | gtgcatttca | gacgggctgt | gctgaacact | gcagcttgaa | 1020 |
| tgagaatatc | actgtcccag | acaccaaagt | taatttctat | gcctggaaga | ggatggaggt | 1080 |
| gagttccttt | ttttttttttt | ttcctttctt | tggagaatc | tcatttgcga | gcctgatttt | 1140 |
| ggatgaaagg | gagaatgatc | gggggaaagg | taaaatggag | cagcagagat | gaggctgcct | 1200 |
| gggcgcagag | gctcacgtct | ataatcccag | gctgagatgg | ccgagatggg | agaattgctt | 1260 |
| gagccctgga | gtttcagacc | aacctaggca | gcatagtgag | atccccatc | tctacaaaca | 1320 |
| tttaaaaaaa | ttagtcaggt | gaagtggtgc | atggtggtag | tcccagatat | ttggaaggct | 1380 |
| gaggcgggag | gatcgcttga | gcccaggaat | ttgaggctgc | agtgagctgt | gatcacacca | 1440 |
| ctgcactcca | gcctcagtga | cagagtgagg | ccctgtctca | aaaagaaaa | gaaaaagaa | 1500 |
| aaataatgag | ggctgtatgg | aatacattca | ttattcattc | actcactcac | tcactcattc | 1560 |
| attcattcat | tcattcaaca | agtcttattg | cataccttct | gtttgctcag | cttggtgctt | 1620 |
| ggggctgctg | agggcagga | gggagaggt | gacatgggtc | agctgactcc | cagagtccac | 1680 |
| tccctgtagg | tcgggcagca | ggccgtagaa | gtctggcagg | gcctggccct | gctgtcggaa | 1740 |
| gctgtcctgc | ggggccaggc | cctgttggtc | aactcttccc | agccgtggga | gccctgcag | 1800 |
| ctgcatgtgg | ataaagccgt | cagtggcctt | cgcagcctca | ccactctctt | cgggctctgg | 1860 |
| gagcccaggt | gagtaggagc | ggacacttct | gcttgccctt | tctgtaagaa | ggggagaagg | 1920 |
| gtcttgctaa | ggagtacagg | aactgtccgt | attccttccc | tttctgtggc | actgcagcga | 1980 |
| cctcctgttt | tctccttggc | agaaggaagc | catctcccct | ccagatgcgg | cctcagctgc | 2040 |
| tccactccga | acaatcactg | ctgacacttt | ccgcaaactc | ttccgagtct | actccaattt | 2100 |

```
                                    -continued cctccgggga aagctgaagc tgtacacagg ggaggcctgc aggacagggg acagatgaaa     2160
gctt                                                                  2164

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 5
gaattccatg ggggtgcacg aatgtcc                                           27
```